US010874012B2

(12) United States Patent
Kaneko et al.

(10) Patent No.: US 10,874,012 B2
(45) Date of Patent: Dec. 22, 2020

(54) BIOSAFETY CABINET AND CLEAN AIR DEVICE

(71) Applicant: Hitachi Industrial Equipment Systems Co., Ltd., Tokyo (JP)

(72) Inventors: Takeshi Kaneko, Tokyo (JP); Hirotoshi Sato, Tokyo (JP)

(73) Assignee: Hitachi Industrial Equipment Systems Co., Ltd., Tokyo (JP)

(*) Notice: Subject to any disclaimer, the term of this patent is extended or adjusted under 35 U.S.C. 154(b) by 190 days.

(21) Appl. No.: 16/325,242

(22) PCT Filed: Apr. 24, 2017

(86) PCT No.: PCT/JP2017/016183
§ 371 (c)(1),
(2) Date: Feb. 13, 2019

(87) PCT Pub. No.: WO2018/073995
PCT Pub. Date: Apr. 26, 2018

(65) Prior Publication Data
US 2019/0208613 A1 Jul. 4, 2019

(30) Foreign Application Priority Data
Oct. 19, 2016 (JP) ................................ 2016-204795

(51) Int. Cl.
*H05F 3/06* (2006.01)
*C12M 1/12* (2006.01)
(Continued)

(52) U.S. Cl.
CPC .............. *H05F 3/06* (2013.01); *A61G 10/00* (2013.01); *B01L 1/04* (2013.01); *B01L 1/50* (2013.01);
(Continued)

(58) Field of Classification Search
USPC .................................................. 361/220, 230
See application file for complete search history.

(56) References Cited

U.S. PATENT DOCUMENTS

2008/0150404 A1* 6/2008 Ono ......................... B25H 1/20
312/209
2018/0264459 A1* 9/2018 Oguma ................. F24F 3/1607

FOREIGN PATENT DOCUMENTS

| CN | 205435809 U | 8/2016 |
|---|---|---|
| JP | 61-96342 A | 5/1986 |

(Continued)

OTHER PUBLICATIONS

International Search Report (PCT/ISA/210) issued in PCT Application No. PCT/JP2017/016183 dated Jun. 27, 2017 with English translation (five (5) pages).

(Continued)

*Primary Examiner* — Danny Nguyen
(74) *Attorney, Agent, or Firm* — Crowell & Moring LLP

(57) ABSTRACT

The purpose of the present invention is to provide a clean air device that can reduce the risk of contamination due to static electricity. Provided is a biosafety cabinet or a clean air device that connects a biosafety cabinet and a clean booth, wherein a static eliminator (ionizer) that generates a corona discharge by way of concentrating an electric field on a needle-shaped discharge electrode and eliminates static with ionized air is disposed directly above an air flow branching point where air supplied to a work space branches to the front face and to rear face inside the biosafety cabinet.

6 Claims, 6 Drawing Sheets

(51) Int. Cl.
*B01L 1/00* (2006.01)
*A61G 10/00* (2006.01)
*F24F 3/16* (2006.01)
*F24F 7/06* (2006.01)
*B01L 1/04* (2006.01)
*B01D 46/42* (2006.01)

(52) U.S. Cl.
CPC ............... *C12M 37/00* (2013.01); *F24F 3/16* (2013.01); *F24F 7/06* (2013.01); *B01D 46/4209* (2013.01); *B01D 2279/51* (2013.01); *B01L 2200/082* (2013.01); *B01L 2200/085* (2013.01)

(56) References Cited

FOREIGN PATENT DOCUMENTS

| | | |
|---|---|---|
| JP | 2006-43521 A | 2/2006 |
| JP | 2011-147842 A | 8/2011 |
| JP | 2014-73457 A | 4/2014 |

OTHER PUBLICATIONS

Japanese-language Written Opinion (PCT/ISA/237) issued in PCT Application No. PCT/JP2017/016183 dated Jun. 27, 2017 (four (4) pages).

Japanese-language Office Action issued in counterpart Japanese Application No. 2018-546141 dated Oct. 8, 2019 with English translation (six (6) pages).

\* cited by examiner

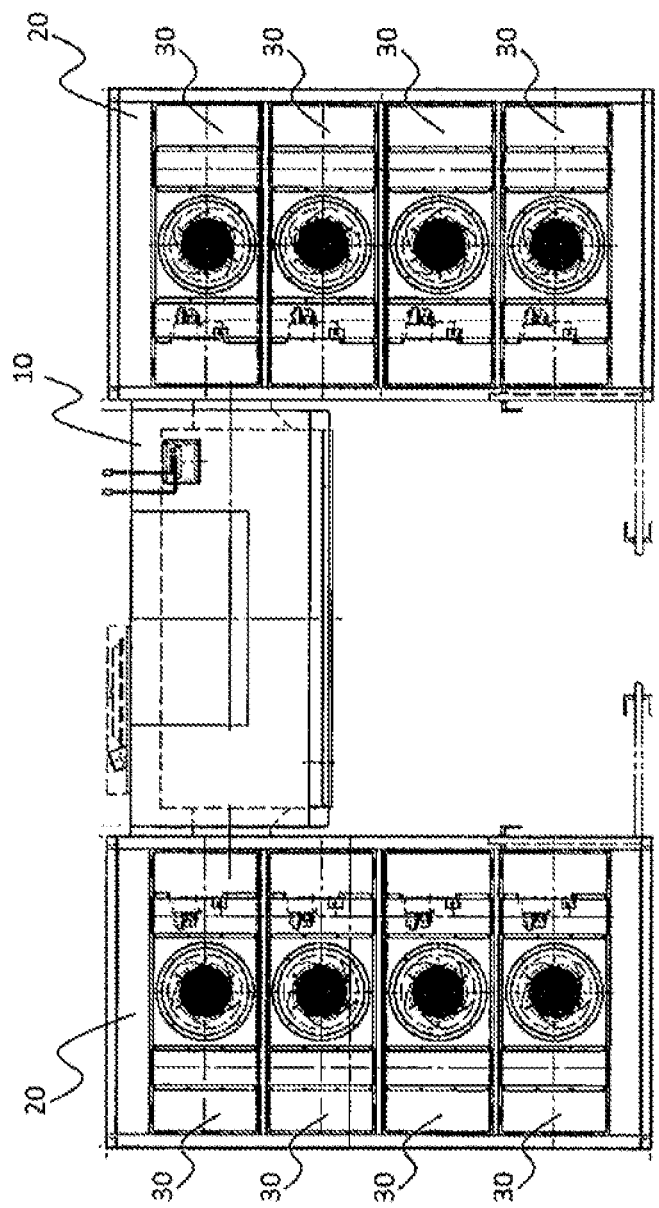

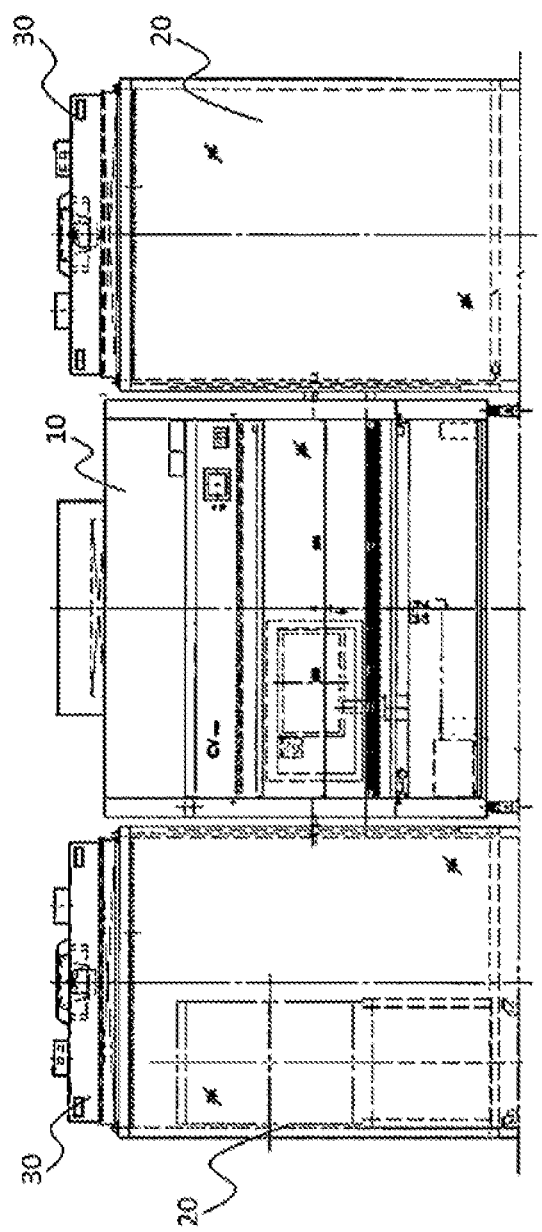

BIOSAFETY CABINET AND CLEAN AIR DEVICE

TECHNICAL FIELD

This application is based upon and claims the benefit of priority of the prior Japanese Patent Application No. 2016-204795 filed on Oct. 19, 2016, the entire contents of which are incorporated herein by reference.

The present invention relates to a biosafety cabinet and a clean air device in the industrial fields of regenerative medicine, medical care, pharmaceuticals and the like.

BACKGROUND ART

Conventionally, a biosafety cabinet has been used as a measure to counter biohazards, while a clean air device such as a clean bench and a clean booth has been used to secure a locally clean space. The clean air device has an isolation capability of protecting a specimen from external bacteria, by performing work in a partitioned space which is provided with an air barrier and includes an opening in a part thereof.

Meanwhile, regenerative medicine is drawing attention in recent years, and therefore there is a growing demand that a series of movements of a cell culture container such as cell culture, medium change, cell observation and packing is realized in clean air whose cleanliness level is so high as to correspond to Grade A to eliminate contamination risk.

As the background art in this technical field, there is JP 2006-043521A (Patent Literature 1). An object of Patent Literature 1 is to provide a biosafety cabinet as a measure to counter biohazards with a simplified connecting structure through which an infectious material under experiment can be transferred, without being taken out of a work space of the biosafety cabinet, to another biosafety cabinet, and to provide a biosafety cabinet in which a connecting part structure of a connected type of biosafety cabinet is simplified, and bacteria/viruses is prevented by pressure control. To this end, multiple connected biosafety cabinets are disclosed in which circulation passages of the connected biosafety cabinets are connected together to be the same space, and a connecting part passing space is configured in the shared circulation passage in the form of connecting the work spaces of the multiple biosafety cabinets (see Abstract).

CITATION LIST

Patent Literature

PATENT LITERATURE 1: JP 2006-043521A

SUMMARY OF INVENTION

Technical Problem

According to Patent Literature 1, the work spaces of the two biosafety cabinets are connected together; a connecting part passing space is formed in that connecting part; and the connecting part passing space is formed in a shared negatively-pressurized contamination plenum. This reduces the possibility that bacteria/viruses may leak from the connecting part passing space to the outside of the biosafety cabinets.

Patent Literature 1, however, pays no attention to dielectrifying (or eliminating static) in the biosafety cabinet, or in the connecting part between the connected biosafety cabinets. For example, in the regenerative medicine field, cell manipulation such as cell culture and culture need to be performed. In a case where the cell manipulation is performed in a biosafety cabinet and the culture is performed in a clean booth, it is considered that the biosafety cabinet and the clean booth are connected together to deliver a cell culture container therebetween for the purpose of eliminating contamination risk. In this case, an operator enters the clean booth in which various equipment is handled, while manual operation using electrically-insulated objects such as a Petri dish, a bottle, a pipette, and other plastic tools is involved in the biosafety cabinet, and therefore static electricity may be caused. Thus, there is likelihood that: an object electrostatically charged during the operation is attracted to the hands; and waste matters having been once inputted in a waste can placed inside the biosafety cabinet float due to electrostatically charge. In addition, if electrostatically-charged dust attached to the equipment enters the biosafety cabinet, such dust causes specimen contamination.

In view of the above-mentioned situation, an object of the present invention is to reduce the contamination risk due to static electricity and secure workability in a biosafety cabinet, or in a clean air device in which the biosafety cabinet and a clean booth are connected together.

Solution to Problem

An outline of an exemplary invention, among the inventions disclosed in the present application, will be briefly described as follows.

It is a biosafety cabinet including: a work space formed on an inner surface side of a front shutter; a circulation passage formed from a lower surface side, a lateral surface side and a rear surface side of the work space, and an outer part of the biosafety cabinet to discharge air having flown into the work space; and an air supplier disposed on an upper surface of the work space for supplying air to the work space, characterized in that an ionizer is provided right above an airflow branch point where the air supplied to the work space branches toward a front surface and a rear surface of the biosafety cabinet.

Advantageous Effects of Invention

The present invention makes it possible to reduce contamination risk due to static electricity and secure workability in a biosafety cabinet, or in a clean air device in which the biosafety cabinet and a clean booth are connected.

The other problems, features and effects will be clarified by the following descriptions of embodiments.

BRIEF DESCRIPTION OF DRAWINGS

FIG. 1A is a plan view illustrating an overall configuration of a clean air device including a biosafety cabinet and clean booths according to Embodiment 1.

FIG. 1B is a front view illustrating the overall configuration of the clean air device including the biosafety cabinet and the clean booths according to Embodiment 1.

DESCRIPTION OF EMBODIMENTS

Figure 2:
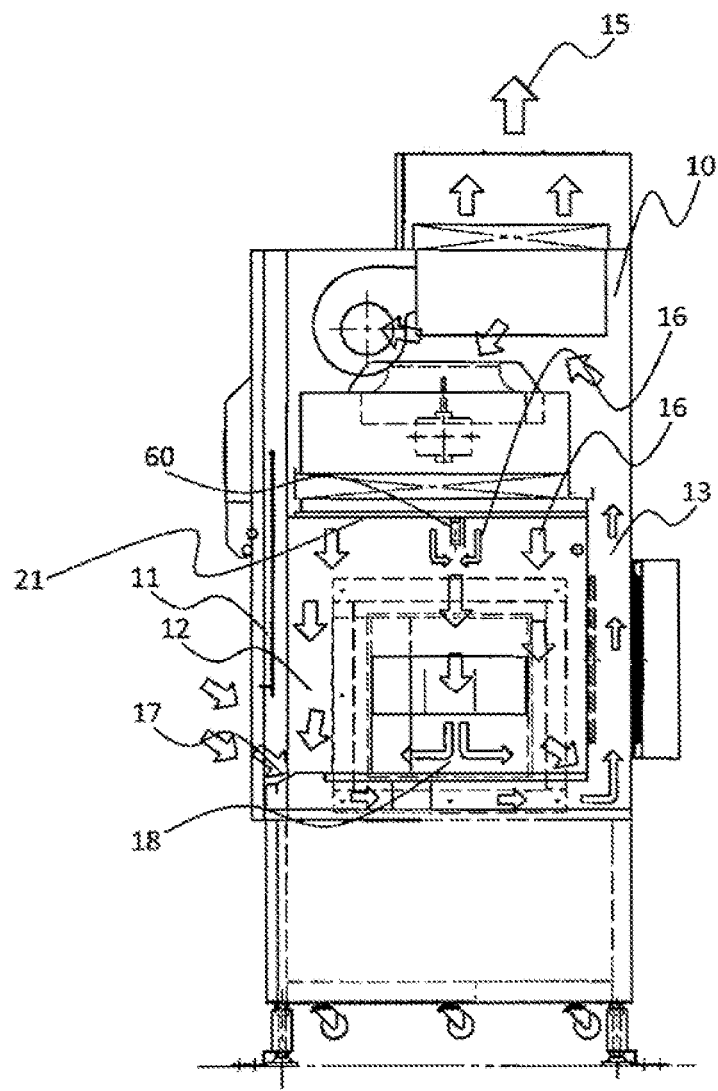
FIG. 2 is an image diagram of an airflow in a center cross section of a right side surface of the biosafety cabinet according to Embodiment 1.

Hereinafter, descriptions will be provided for embodiments of the present invention referring to the drawings.

It should be noted that the embodiments will be described by being divided into multiple sections or embodiments, as needed for convenience. However, those are not irrelevant to one another unless otherwise indicated, but have relationships such as modifications, details, supplementary explanations in which one is a part or the whole of the other.

Further, in the following embodiments, when the number and the like of elements (including a quantity, numerical value, amount, range, and the like) are mentioned, those are not limited to the specific number unless otherwise specifically indicated or unless obviously limited to the specific number from a principle viewpoint, but may be equal to, greater than, or less than the specific number.

Furthermore, in the following embodiments, it is a matter of course that components (including elemental steps or the like) are not necessarily essential unless otherwise specifically indicated or unless obviously considered essential from a principle viewpoint.

Likewise, in the following embodiments, when a shape, positional relation and the like of the components and the like are mentioned, those include what are substantially close to or similar to the shape and the like unless otherwise specifically indicated or unless obviously considered otherwise from a principle viewpoint. This also applies to the numerical values and ranges as well.

In all drawings for describing the embodiments, the same reference signs are given to members having the same functions, so that duplicated descriptions are omitted.

Embodiment 1

This embodiment describes an example which reduces contamination risk due to electrification and secure workability by disposing only one ionizer in a biosafety cabinet efficiently to effectively exert an effect of diselectrifying.

FIGS. 1A and 1B are diagrams illustrating an overall configuration of a clean air device consisting of a biosafety cabinet and clean booths. FIG. 1A shows a plan view, and FIG. 1B shows a front view, in which reference sign 10 denotes a biosafety cabinet, reference sign 20 denotes a clean booth, and reference sign 30 denotes a fan filter unit (FFU). The biosafety cabinet 10 is a device into which only an arm of an operator moves is inserted for performing manipulation of a cell, such as cell culture. The clean booth 20 is a culture or centrifuge booth, or an acceptance base material booth, and is a space in which an operator works. The FFU 30 is a unit with a fan and a filter installed in a housing, and cleans air taken therein by using the fan, through HEPA filters, to deliver it as clean air. Furthermore, the biosafety cabinet 10 and the clean booth 20 are connected to each other through a pass box 40 (see FIG. 4B). The pass box 40 is provided with a connecting opening in a part of a side surface wall of a work space 12, and is constructed so that a material or specimen which may be infected can be delivered from the work space 12 in the biosafety cabinet 10 to the clean booth 20 without being taken out of the biosafety cabinet. The pass box 40 includes a pass box door 41, and a passage between the pass box and the clean booth 20 can be blocked by closing the pass box door 41.

FIG. 2 is an image diagram of a center cross sectional view of a right side surface of the biosafety cabinet according to this embodiment. In FIG. 2, the biosafety cabinet 10 includes: a front shutter 11; the work space 12 formed on an inner surface side of the front shutter 11 to hold a negatively-pressurized state; and a circulation passage 13 formed by a lower surface side, a lateral surface side and a rear surface side of the work space 12 and an outer part of a main body of the biosafety cabinet 10 to discharge air flowing into the work space 12. The operator inserts an arm from a front opening of the biosafety cabinet 10, and performs operation of cell manipulation in the work space while looking into the work space 12 from the front shutter 11. The front opening is a space between an lower end of the front shutter 11 and a front grill 17.

In FIG. 2, a stream of an airflow will be described. In the biosafety cabinet 10, the air sucked through the front opening passes through the circulation passage 13 at a lower portion, a rear surface portion and a side surface portion of the work space 12, and is thereafter sucked into a blower (not shown). A part of the air sucked into the blower is filtered by a circulation HEPA filter (not shown) and is discharged into the work space 12 as clean air, while the other part of the air is filtered by an exhaust HEPA filter (not shown) and is discharged to the outside of the biosafety cabinet 10 as clean air as a biosafety cabinet exhaust airflow 15. A biosafety cabinet blow-out airflow 16 is supplied into the work space 12 through a blow-out punching plate (perforated plate) 21 disposed on the upper surface of the work space 12. The biosafety cabinet blow-out airflow 16 cleans the interior of the work space 12. A part of the biosafety cabinet blow-out airflow 16 is sucked through the front grill 17 while the other part of the biosafety cabinet blow-out airflow 16 is sucked through a biosafety cabinet rear surface slit 14 (described below), and then the biosafety cabinet blow-out airflow 16 passes through the circulation passage 13 and is sucked into the blower.

Here, the embodiment is characterized in that an ionizer 60 is disposed right above an airflow branch point 18 where the biosafety cabinet blow-out airflow 16 in the work space 12 separates toward the front and the rear near a working table 19.

Thereby, ions generated from an electrode probe of the ionizer spreads to the work space 12 while flowing together with the biosafety cabinet blow-out airflow 16, and separates toward the front and the rear at the airflow branch point 18 to flow to equipment and specimens on the working table 19, so that it is possible to efficiently perform diselectricitying of the entire working table 19.

Because the airflow branch point 18 is a point where the biosafety cabinet blow-out airflow 16 separates toward the front and the rear near the working table 19, the airflow branch point 18 becomes stagnant there. However, by disposing the ionizer 60 right above the airflow branch point, an airflow from the surroundings whirls right below the ionizer 60 so that the velocity of wind right below the ionizer 60 becomes higher than the surroundings. Thereby, the stagnancy of the airflow is cleared, and also there is an effect that the dust involved in the operation in the work space 12 can be efficiently emitted.

Embodiment 2

This embodiment describes an example which effectively performs dielectrifying of an input port of the waste can in a case where the waste can is placed on the working table in the biosafety cabinet.

Figure 3A:
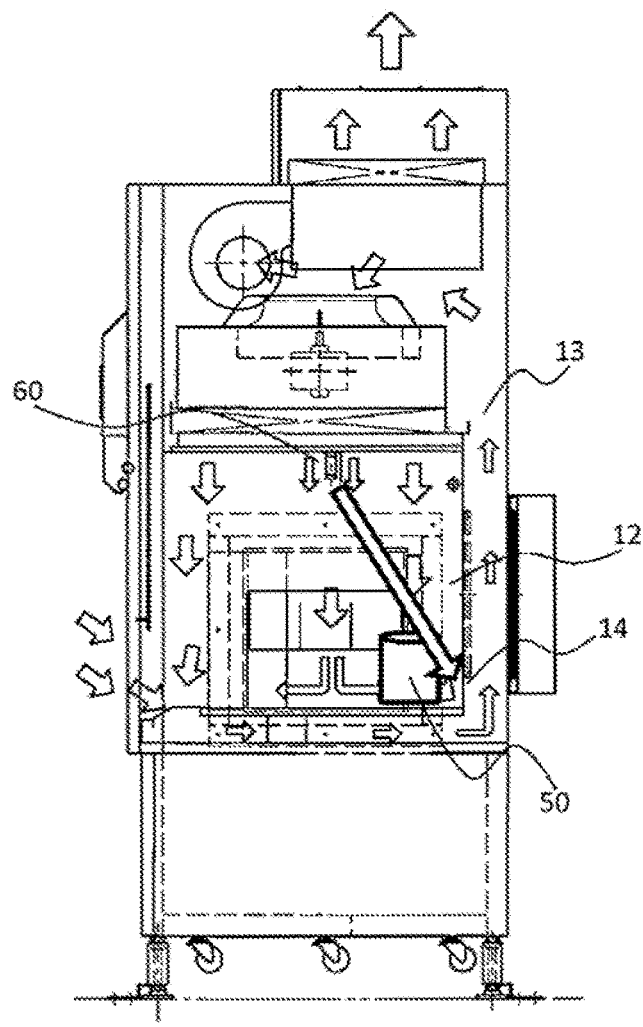
FIG. 3A is a view of a right side surface of a biosafety cabinet according to Embodiment 2.
Figure 3B:
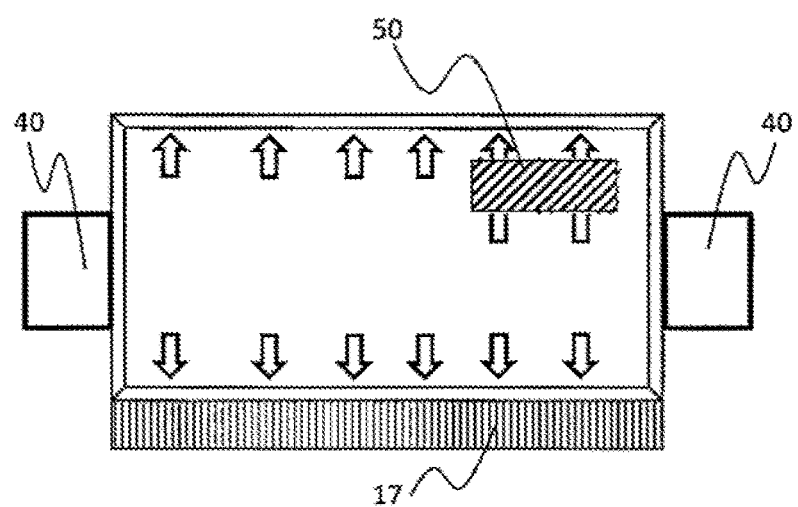
FIG. 3B is a cross-sectional plan view of a work space of the biosafety cabinet according to Embodiment 2.

FIG. 3A is a right side view of the biosafety cabinet 10 in this embodiment, where the waste can 50 is placed in the work space 12. FIG. 3B is a plan view of the working table 19 of the biosafety cabinet 10 illustrated in FIG. 3A.

In FIG. 3A, the ionizer 60 is arranged at the same place as Embodiment 1. This embodiment is characterized in that the input port of the waste can 50 is arranged in a straight line joining the electrode probe of the ionizer 60 and the biosafety cabinet rear surface slit 14. In other words, the embodiment is characterized in that a rear surface slit is provided at a lower end of the rear surface of the biosafety cabinet in in a general, while another rear surface slit than the above rear surface slit is newly provided at a height near the input port of the waste can 50.

The waste can 50 is provided for temporarily accommodating waste matters generated by work in the work space 12, and is a SUS can or a bag made from polyethylene or the like. In a case where the waste matters are frequently generated, an exhaust port is often left open and is not closed by a lid. A bag made from polyethylene or the like which had been accommodated a pipette or the like used in the work, or waste cloth or the like which had been used for cleaning is disposed therein. However, due to friction electrification involved in the work, or peeling electrification caused when opening a bag accommodating equipment, the waste matters inputted in the waste can sometimes come to float out of the waste can, and the waste matters are sometimes attracted to a hand when disposing in the waste can. By locating the waste can 50 at the above-mentioned place, the dielectrifying effect of the ionizer can be brought about also at the input port of the waste can 50, so that the causes of contamination like the above-mentioned phenomena can be prevented.

Embodiment 3

This embodiment describes an example which enhances the dielectrifying effect in the pass box in the clean air device in which the biosafety cabinet and the clean booths are connected with each other.

Figure 4A:
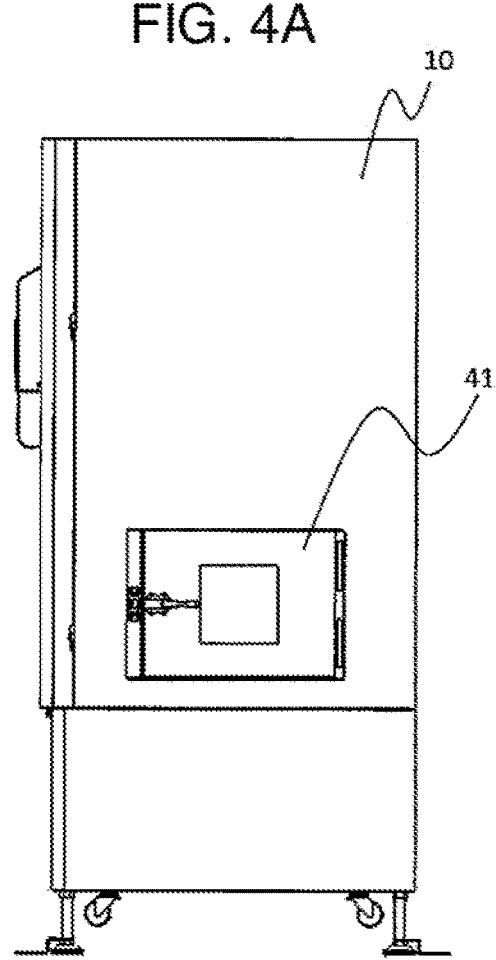
FIG. 4A is a view of a right side surface of a biosafety cabinet according to Embodiment 3.
Figure 4B:
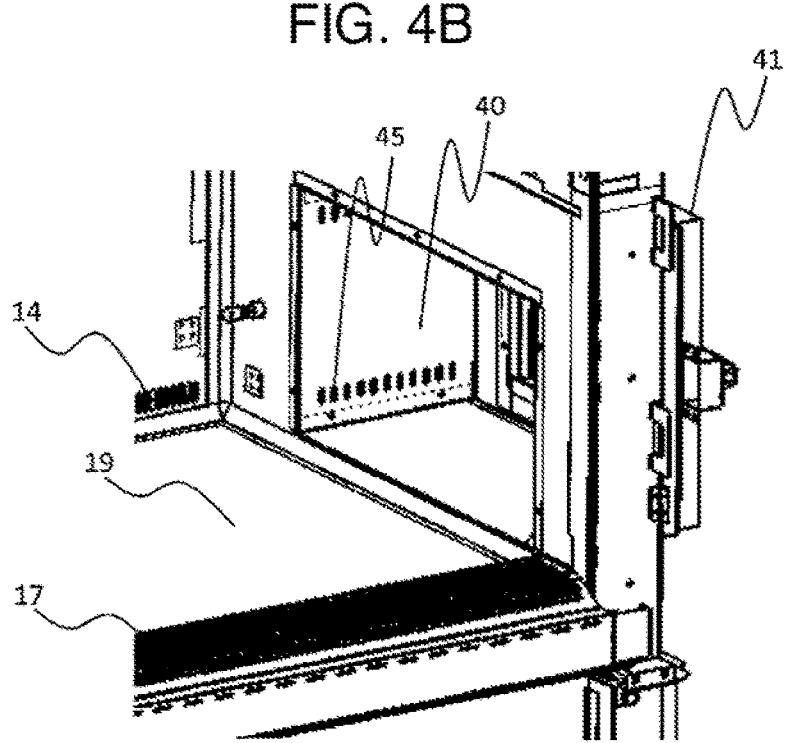
FIG. 4B is a cross-sectional perspective view of the biosafety cabinet according to Embodiment 3.

FIG. 4A shows a right side view of the biosafety cabinet 10 in this embodiment, and FIG. 4B shows a cross-sectional perspective view.

As shown in FIG. 4B, this embodiment is characterized in that a pass box connecting part inner surface slit 45 is provided in the pass box. The biosafety cabinet blow-out airflow 16 thereby spreads toward the left and right pass boxes 40 in the work space 12, so that the dielectrifying of the pass boxes 40, particularly of the entire bottom surfaces of the pass boxes becomes possible. Accordingly, when putting the equipment or specimen into the biosafety cabinet from the clean booth side, it is possible to dielectrify and peel off the dust adhering thereto due to electrification, and emit it from the pass box connecting part inner surface slits 45. Therefore, it is possible to inhibit bringing-in of the dust into the work space 12 of the biosafety cabinet 10 to maintain the cleanliness.

Embodiment 4

This embodiment describes an example which further enhances the dielectrifying effect in the pass box in the clean air device in which the biosafety cabinet and the clean booths are connected with each other.

Figure 5:
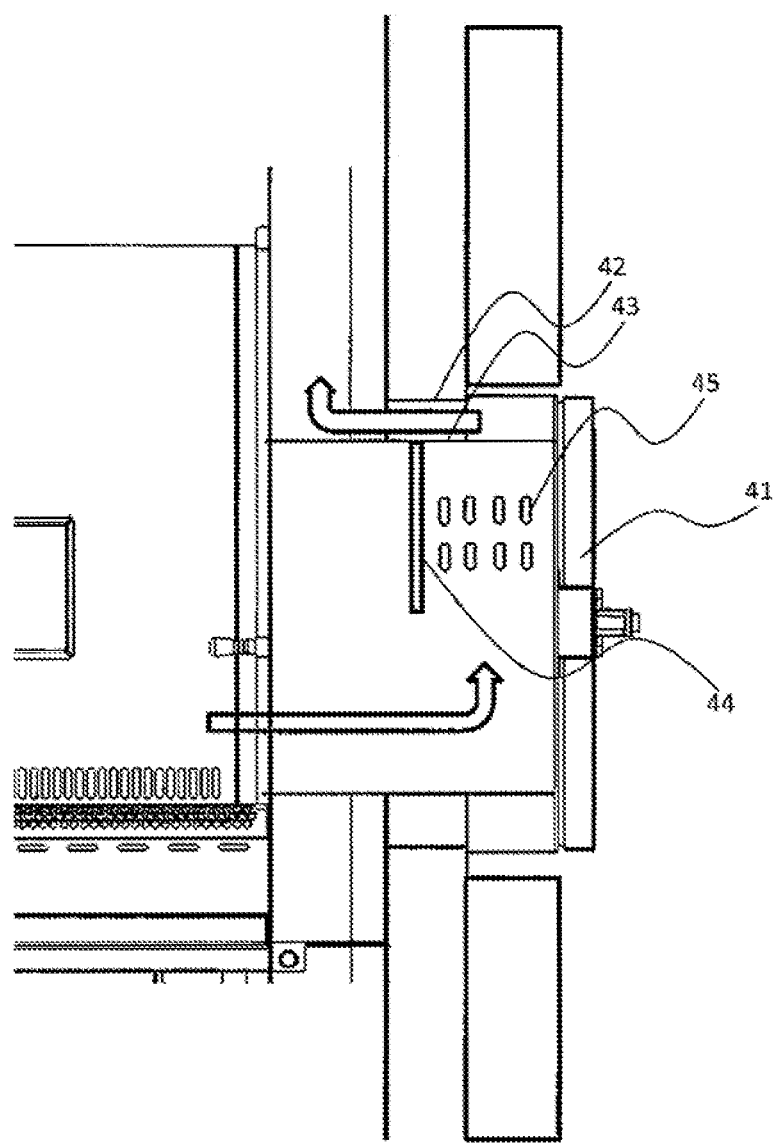
FIG. 5 is a vertical cross-sectional view of a periphery of a pass box which is a connecting part between a biosafety cabinet and a clean booth according to Embodiment 4, seen from the front thereof.

FIG. 5 is a vertical cross-sectional view of the circumference of the pass box 40 seen from the front that is a connecting part between the biosafety cabinet and the clean booth in this embodiment. The characteristics are that: a partition curtain 44 is provided on the upper surface of the pass box around the center thereof; and the pass box connecting part inner surface slits 45 are provided on the pass box door 41 side with respect to the curtain 44 and above the lowermost part of the curtain 44. Note that the workability is good when the curtain 44 is made from transparent glass, translucent silicone or the like.

By these features, even if the equipment or specimen is electrostatically charged when being introduced from the clean booth 20, the dielectrifying is carried out only by putting it on the bottom of the pass box 40 under the favor of the dielectrifying effect of the ionizer 60 disposed in the biosafety cabinet 10, and the dust peeled by the dielectrifying can be emitted from the pass box connecting part inner surface slits 45 through the circulation passage 13. Further, since the biosafety cabinet blow-out airflow 16 passes through the pass box 40, and is emitted from the pass box connecting part inner surface slits 45, there is also an effect of maintaining the cleanliness of the entire pass box 40.

Note that although the examples of the biosafety cabinet and the clean air device are described in the above embodiments, it is possible to consider the embodiments as an example of a clean room by arranging those in the clean room.

Although the above descriptions have been made for the embodiments, it is clear to those skilled in the art that the present invention is not limited thereto, and can be variously modified and changed within the scope of the spirit of the present invention and the appended claims.

REFERENCE SIGNS LIST 10 biosafety cabinet
11 front shutter
12 work space
13 circulation passage
14 biosafety cabinet rear surface slit
15 biosafety cabinet exhaust airflow
16 biosafety cabinet blow-out airflow
17 front grill
18 airflow branch point
19 working table
20 clean booth
21 blow-out punching plate
30 FFU
40 pass box
41 pass box door
42 pass box connecting part outer surface
43 pass box connecting part inner surface
44 pass box connecting part curtain
45 pass box connecting part inner surface slit
50 waste can
60 ionizer

The invention claimed is:

1. A biosafety cabinet comprising:
   a work space formed on an inner surface side of a front shutter;
   a circulation passage formed from a lower surface side, a lateral surface side and a rear surface side of the work space, and an outer part of the biosafety cabinet for discharging air having flown into the work space, and an air supplier disposed on an upper surface of the work space for supplying air to the work space, characterized in that an ionizer is provided right above an airflow branch point where the air supplied to the work space branches toward a front surface and a rear surface of the biosafety cabinet.

2. The biosafety cabinet according to claim 1, characterized in that a working table is disposed on a lower surface of the work space, and the airflow branch point is a point where the air supplied to the work space branches toward the front surface and the rear surface of the biosafety cabinet near the working table.

3. The biosafety cabinet according to claim 1, characterized in that an input port of a waste can is arranged in a straight line joining the ionizer and a rear surface slit of the biosafety cabinet.

4. The biosafety cabinet according to claim 1, characterized in that the biosafety cabinet includes a first rear surface slit, and a second rear surface slit located at a predetermined height from the first rear surface slit.

5. A clean air device comprising:

the biosafety cabinet according to claim 1;

a clean booth; and a pass box connecting the clean booth and the biosafety cabinet, characterized in that a slit is provided in the pass box.

6. The clean air device according to claim 5, characterized in that a partition member is provided at a central part on an upper surface of the pass box, and the slit is provided at an upper portion on a closer side to the clean booth than the partition member in the pass box.

* * * * *